United States Patent
MacLeod et al.

Patent Number: 5,661,162
Date of Patent: Aug. 26, 1997

[54] 4-AMINOMETHYL/THIOMETHYL/ SULFONYLMETHYL-4-PHENYLPIPERDINES AS TACHYKININ RECEPTOR ANTAGONISTS

[75] Inventors: Angus Murray MacLeod, Bishops Stortford; Graeme Irvine Stevenson, Saffron Walden, both of United Kingdom

[73] Assignee: Merck Sharp & Dohme Limited, Harlow Essex, England

[21] Appl. No.: 448,622

[22] PCT Filed: Dec. 10, 1993

[86] PCT No.: PCT/GB93/02535

§ 371 Date: Jun. 6, 1995

§ 102(e) Date: Jun. 6, 1995

[87] PCT Pub. No.: WO94/13639

PCT Pub. Date: Jun. 23, 1994

[30] Foreign Application Priority Data

Dec. 14, 1992 [GB] United Kingdom ............... 9226014
Jul. 2, 1993 [GB] United Kingdom ............... 9313726
Jul. 12, 1993 [GB] United Kingdom ............... 9314486

[51] Int. Cl.$^6$ .............. A61K 31/445; C07D 211/26
[52] U.S. Cl. .............. 514/331; 514/330; 546/226; 546/229; 546/232; 546/236
[58] Field of Search ............... 514/311–314, 316–318, 514/322, 326, 329, 331; 546/153, 155, 176, 177, 194, 199, 207–210, 213, 214, 216, 223, 226, 229, 230, 232, 234, 235–237, 239

[56] References Cited

U.S. PATENT DOCUMENTS

| | | | |
|---|---|---|---|
| 2,538,107 | 1/1951 | Kwartler et al. | 546/231 |
| 2,773,870 | 12/1956 | Elpern | 544/129 |
| 3,083,205 | 3/1963 | Janssen et al. | 546/234 |

FOREIGN PATENT DOCUMENTS

| | | |
|---|---|---|
| 640941 | 6/1964 | Belgium . |
| 0512902 | 11/1992 | European Pat. Off. . |
| 0512901 | 11/1992 | European Pat. Off. . |
| 1381445 | 11/1964 | France . |
| 1501151 | 11/1967 | France . |
| 1356118 | 6/1974 | United Kingdom . |
| WO92/01672 | 2/1992 | WIPO . |
| WO92/12128 | 7/1992 | WIPO . |

OTHER PUBLICATIONS

Naranjo, J.R. et al, Eur. J. Pharmacol. 1984(Feb. 10), 98(1), pp. 133–136.
Archiv. Pharm., 319(6), 505–515 (1986), "4–Piperidinyl-methanamine".
Chemical Abstracts, 60(9), AB. No. 11242h, (Apr. 27,1964).
Chemical Abstracts, 62(8), AB. No. 9114c, (Apr. 12, 1965).
Chemical Abtracts, 89(5), AB. No. 43033t, (Jul. 31, 1978).
Chemical Abstracts, 86(13), AB. No. 89539d, (Mar. 28, 1977).
Chemical Abstracts, 94, (23), AB. No. 192068p, (Jun. 8, 1981).
Journ. of Med. Chem., 10(2) 174–177 (1967) "Histamine Releasers . . . ".

Primary Examiner—C. Warren Ivy
Assistant Examiner—Garth M. Dahler
Attorney, Agent, or Firm—J. Eric Thies; David L. Rose

[57] ABSTRACT

The present invention is directed to compounds of the formula (I)

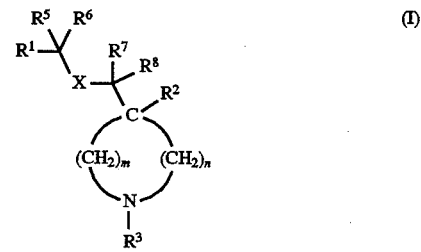

wherein $R^1$, $R^2$, $R^3$, $R^5$, $R^6$, $R^7$, $R^8$, m, n and X are defined herein, and pharmaceutically acceptable salts thereof, which are useful as tachykinin antagonists.

13 Claims, No Drawings

4-AMINOMETHYL/THIOMETHYL/ SULFONYLMETHYL-4-PHENYLPIPERDINES AS TACHYKININ RECEPTOR ANTAGONISTS

This application is the U.S. national stage application of PCT/GB93/02535 filed Dec. 10, 1993 which is published as WO 94/13639 on Jun. 23, 1994.

This invention relates to a class of azacyclic compounds, which are useful as tachykinin antagonists. More particularly, the compounds of the invention comprise an azacyclic ring system substituted by an arylmethylamino moiety.

The tachykinins are a group of naturally-occurring peptides found widely distributed throughout mammalian tissues, both within the central nervous system and in the peripheral nervous and circulatory systems. The three known mammalian tachykinins are as follows:
Substance P;
Neurokinin A;
Neurokinin B;

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of formula (I), or a salt or prodrug thereof:

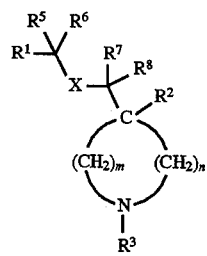

wherein
x is $NR^4$ or SO or $SO_2$
m is 2, 3 or 4;
n is 0, 1 or 2 when m is 2 or 3, and n is 0 or 1 when m is 4;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$, where $R^a$ and $R^b$ each independently represent H, $C_{1-6}$alkyl, phenyl or trifluoromethyl; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, CONHphenyl($C_{1-4}$alkyl), $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), $Y$—$R^{16}$ or CO—Z—($CH_2)_q$—$R^{12}$;

$R^4$ represents H, $C_{1-6}$alkyl or $COR^9$.
$R^5$, $R^6$, $R^7$ and $R^8$ each independently represent H or $C_{1-6}$alkyl; or when X is $NR^4$, either $R^5$ and $R^6$ may together represent an oxygen atom or $R^7$ and $R^8$ may together represent an oxygen atom;

$R^9$ represents H, $C_{1-6}$alkyl or phenyl;
$R^{10}$ and $R^{11}$ each independently represent H or $C_{1-6}$alkyl;
$R^{12}$ represents $NR^{13}R^{14}$ or an optionally substituted aromatic or non-aromatic azacyclic or azabicyclic group;
$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenylCl$_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, trifluoromethyl or phenyl optionally substituted by one or more substituents selected from $C_{1-6}$alkyl, $C_{1-6}$alkoxy, halo and trifluoromethyl;

$R^{16}$ represents an optionally substituted aromatic heterocycle;

Y represents a hydrocarbon chain of 1,2,3 or 4 carbon atoms which may optionally be substituted by oxo;

Z represents $CH_2$, O, S or $NR^{10}$; and
q represents 0, 1, 2, 3, 4, 5 or 6.

As used herein, the definition of each expression, when it occurs more than once in any structure, is intended to be independent of its definition elsewhere in the same structure.

The alkyl, alkenyl and alkynyl groups referred to with respect to the formulae herein may represent straight, branched or cyclic groups, or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985. Preferably the compound of the formula (I) is the free base or a pharmaceutically acceptable acid addition salt thereof.

Those compounds according to the invention which contain one or more chiral centres may exist both as enantiomers and as diastereomers. It is to be understood that all such isomers and mixtures thereof are encompassed within the scope of the present invention.

In one apt group of compounds of the invention X is SO or $SO_2$.

In one favoured group of compounds of the invention X is $NR^4$ and $R^5$, $R^6$ $R^7$ and $R^8$ each independently represent H or $C_{1-6}$ alkyl. In this group of compounds suitably $R^5$, $R^6$ $R^7$ and $R^8$ each represent H. In this group of compounds suitably $R^5$ represents methyl and $R^6$, $R^7$ and $R^8$ represent H.

In a further group of compounds of the invention X is $NR^4$ and $R^5$ and $R^6$ together represent an oxygen atom or $R^7$ and $R^8$ represent an oxygen atom.

Preferably m is 2.

When m is 2, n is preferably 2. When m is 3 or 4, n is preferably 0.

Preferably $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy. Preferably $R^1$ represents phenyl substituted by one or more groups selected from $C_{1-6}$alkyl such as methyl or t-butyl, halo such as chloro, fluoro and bromo and trifluoromethyl. One, two or three substituents are typically present.

Preferably $R^1$ represents disubstituted phenyl, in particular 3,5-disubstituted phenyl, for example 3,5-disubstituted phenyl wherein the substituents are selected from $C_{1-6}$alkyl, halo and trifluoromethyl. More preferably $R^1$ represents 3,5-bis(trifluoromethyl) phenyl.

Suitable values for the group $R^2$ include unsubstituted or substituted phenyl, 5-membered heteroaryl such as thienyl, 6-membered heteroaryl such as pyridyl, and benzhydryl.

Preferably $R^2$ represents unsubstituted or substituted phenyl.

When $R^2$ represents substituted phenyl a preferred substituent is halo, especially fluoro.

When $R^{16}$ represents a substituted aromatic heterocycle, suitable substituents in the heterocyclic ring include one or more of $C_{1-6}$alkyl, $C_{1-6}$alkoxy, phenyl, oxo, thioxo, halo, trifluoromethyl, $NR^aR^b$, $NR^aCOR^b$, $CONR^aR^b$, $CO_2R^a$, $SR^a$, $SO_2R^a$ and $CH_2OR^a$, where $R^a$ and $R^b$ are as previously defined. Particular examples of suitable substituents include methyl, methoxy, phenyl, oxo, thioxo, bromo, iodo, $NH_2$, $SCH_3$, $CONH_2$ and cyano. Particularly preferred substituents include oxo and $NH_2$.

Suitable values for $R^{16}$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

Preferably $R^{16}$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably $R^{16}$ represents optionally substituted oxazolyl, oxadiazolyl, imidazolyl, thiadiazolyl, triazolyl, pyrazinyl, pyrimidinyl, pyridazinyl or triazinyl, or tetrazolyl substituted by $C_{1-6}$alkyl, preferably methyl. More preferably $R^{16}$ is an unsubstituted 5-membered nitrogen containing heterocycle or a 5-membered nitrogen containing heterocycle substituted by oxo.

It will be appreciated that, when the heterocyclic moiety $R^{16}$ is substituted by an oxo or thioxo substituent, different tautomeric forms are possible so that the substituent may be represented as =O or —OH, or =S or —SH, respectively. For the avoidance of doubt, all such tautomeric forms are embraced by the present invention.

When $R^{12}$ represents $NR^{13}R^{14}$, $R^{13}$ and $R^{14}$ are preferably both $C_{1-6}$alkyl such as methyl, ethyl, n-propyl, i-propyl, n-butyl, i-butyl or t-butyl. More preferably $R^{13}$ and $R^{14}$ will both represent methyl.

When $R^{12}$ represents an aromatic or non-aromatic azacycle or azabicycle it may contain one or more additional heteroatoms selected from O, S and N or groups $NR^{16}$, where $R^{16}$ is H, $C_{1-6}$alkyl or phenyl$Cl_{1-4}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^{12}$ represents an aromatic azacycle or azabicycle, suitable values of $R^{12}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^{12}$ represents a non-aromatic azacycle or azabicycle, suitable values of $R^{12}$ include morpholinyl, piperdinyl, pyrrolidinyl, piperazinyl, methylpiperazinyl, azanorbornanyl, azabicyclo[2.2.2]octanyl and azabicyclo [3.2.2]nonyl, preferably morpholinyl, methylpiperazinyl, quinuclidinyl (azabicyclo[2.2.2]octanyl) or azabicyclo [3.2.2]nonyl, more preferably quinuclidinyl.

Suitably Y represents a hydrocarbon chain of 1 or 2 carbon atoms optionally substituted by oxo, such as $CH_2$, C=O, $CH(CH_3)$, $CH_2(C=O)$ or $(C=O)CH_2$. Preferably Y represents $CH_2$, $CH(CH_3)$ or $CH_2(C=O)$, more preferably $CH_2$ or $CH(CH_3)$.

Suitably q represents 0, 1, 2 or 3.

Suitable values of $R^3$ include H, $COR^9$ such as $COCH_3$, $SO_2R^{15}$ such as $SO_2CH_3$, $C_{1-6}$alkyl such as $CH_3$, $CH(CH_3)_2$, $CH_2CH(CH_3)_2$ and $CH_2CH_2C(CH_3)_3$, $C_{1-6}$alkyl substituted by $CO_2R^{10}$ such as $CH_2CO_2CH_3$, $CH_2CO_2H$, $(CH_2)_3CO_2CH_3$ and $(CH_2)_3CO_2H$, $C_{1-6}$alkyl substituted by $CONR^{10}SO_2R^{15}$ such as $CH_2CONHSO_2CH_3$ and $CH_2CONHSO_2C_6H_5$, $C_{1-6}$alkyl substituted by phenyl, Y—$R^{16}$ and CO—Z—$(CH_2)_q$—$R^{12}$.

In one preferred subgroup of compounds according to the invention, $R^3$ represents H or $C_{1-6}$alkyl, more preferably H.

In a further preferred subgroup of compounds according to the invention $R^3$ represents $Y-R^{16}$.

Suitable values for $R^4$ include H, methyl and acetyl. Preferably $R^4$ is H or $C(=O)CH_3$, more preferably H.

A particular sub-class of compounds according to the invention is represented by compounds of formula (Ia), and salts and prodrugs thereof:

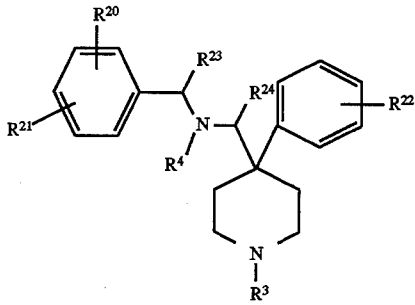
(Ia)

wherein $R^3$ and $R^4$ are as defined for formula (I);

$R^{20}$ and $R^{21}$ independently represent H $C_{1-6}$alkyl, $C_{2-6}$alkenyl, $C_{2-6}$alkynyl, halo, cyano, nitro, trifluoromethyl, trimethylsilyl $OR^a$, $SR^a$ $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined;

$R^{22}$ represents H or halo, preferably H or fluoro; and $R^{23}$ and $R^{24}$ each independently represent H or methyl.

Particular values of $R^{20}$ and $R^{21}$ include H, chloro, bromo, methyl, t-butyl and trifluoromethyl. Preferably $R^{20}$ and $R^{21}$ are both other than H and are located at the 3- and 5-positions of the phenyl ring.

A particular sub-class of compounds according to the invention is represented by compounds of formula (Ib), and salts and prodrugs thereof:

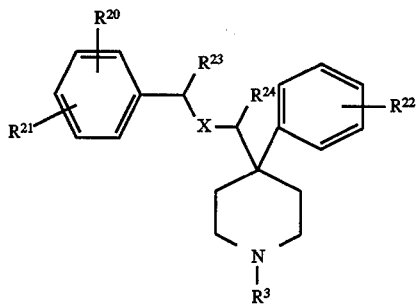
(Ib)

wherein $R^3$ is as defined for formula (I), $X^1$ is SO or $SO_2$;

$R^{20}$ and $R^{21}$ independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $COR^a$ or $CONR^aR^B$, where $R^a$ and $R^b$ are as previously defined;

$R^{22}$ represents H or halo, preferably H or fluoro; and $R^{23}$ and $R^{24}$ each independently represent H or methyl.

Particular values of $R^{20}$ and $R^{21}$ include H, chloro, bromo, methyl, t-butyl and trifluoromethyl. Preferably $R^{20}$ and $R^{21}$ are both other than H and are located at the 3- and 5-positions of the phenyl ring.

A particular sub-class of compounds according to the invention is represented by compounds of formula (Ic), and salts and prodrugs thereof:

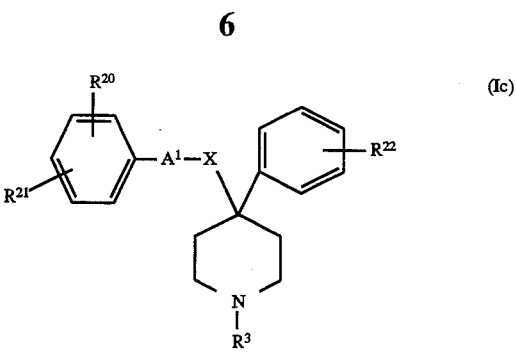
(Ic)

wherein $R^3$ is as defined for formula (I);

$X^2$ is a $C(O=)NR^4CR^6R^7$ or $CR^6R^7NR^4C(O=)$ group;

$R^{20}$ and $R^{21}$ independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined; and $R^{22}$ represents H or halo, preferably H or fluoro.

Aptly X is a $CH_2NR^4C(O=)$, $CH(CH_3)NR^4C(O=)$, $CONR^4CH_2$ or $CONR^4CHCH_3$ group.

Particular values of $R^{20}$ and $R^{21}$ include H, chloro, bromo, methyl, t-butyl and trifluoromethyl. Preferably $R^{20}$ and $R^{21}$ are both other than H and are located at the 3- and 5-positions of the phenyl ring.

Specific compounds within the scope of the present invention include:

4-phenyl-4-(2-methoxybenzylaminomethyl)piperidine;

4-Phenyl-4-(2-Methoxybenzylaminomethyl)piperidine;

4-Phenyl-4-[(3,5-bistrifluoromethylbenzyl)amido] methylpiperidine;

1-t-Butoxycarbonyl-4-phenyl-4-[3,5-bis(trifluoromethyl) benzylthiomethyl]piperidine;

1-t-Butoxycarbonyl-4-phenyl-4-[3,5-bis(trifluoromethyl) benzylsulphinylmethyl]piperidine;

1-t-Butoxycarbonyl-4-phenyl-4-[3,5-bis(trifluoromethyl) benzylsulphonylmethyl]piperidine;

4-Phenyl-4-[3,5-bis(trifluoromethyl) benzylsulphonylmethyl]piperidine;

4-Phenyl-4-[(3,5-bistrifluoromethyl)benzylaminomethyl] piperidine;

4-Phenyl-4-[(3,5-dichloro)benzylaminomethyl]piperidine;

4-Phenyl-4-[(3,5-dichloro)benzylamino-1-ethyl]piperidine;

4-Phenyl-4-[(3-isopropoxy)benzamidomethyl piperidine;

4-Phenyl-4-[(3-isoproxy) N-methyl-benzamidomethyl) piperidine;

and pharmaceutically acceptable salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or. suppositories, for oral, parenteral or rectal administration, or topical administration including administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example, diabetic or chemotherapy-induced neuropathy, and postherpetic and other neuralgias; small cell carcinomas such as small cell lung cancer; respiratory diseases, particularly those associated with excess mucus secretion, such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) for use in therapy. According to a further or alternative aspect, the present invention provides a compound of formula (I) for use in the manufacture of a medicament for the treatment of physiological disorders associated with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds of formula (I) wherein X is $NR^4$ and wherein $R^5$ and $R^6$ are both H, or $R^7$ and $R^8$ are both H may be prepared by a process which comprises reacting a compound of formula (II) with a compound of formula (III):

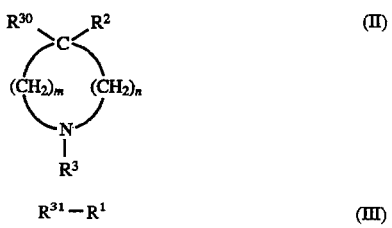

wherein $R^1$, $R^2$, m and n are as defined for formula (I), $R^3$ is as defined for formula (I) except that, when $R^3$ is H it is replaced by a suitable protecting group, such as $CO_2(C_{1-6}alkyl)$, $R^{30}$ is CHO and $R^{31}$ is $CR^5R^6NHR^4$, where $R^4$, $R^5$ and $R^6$ are as defined for formula (I), or $R^{30}$ is $CR^7R^8NHR^4$, where $R^4$, $R^7$ and $R^8$ are as defined for formula (I), and $R^{31}$ is CHO, followed by deprotection, if required.

The reaction is conveniently carried out in a suitable organic solvent, such as a hydrocarbon solvent, e.g. toluene, at elevated temperature, for example, the reflux temperature of the chosen solvent.

Suitably $R^{30}$ represents CHO and $R^{31}$ represents $CR^5R^6NHR^4$.

Alternatively, compounds of formula (I) wherein X is $NR^4$ may be prepared by reaction of compounds of formula (IV) with compounds of formula (V):

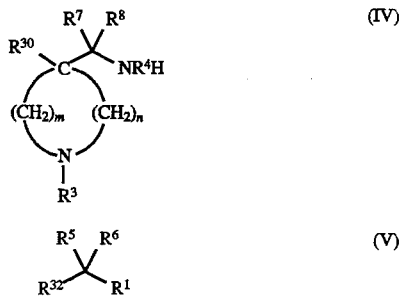

wherein $R^1$, $R^2$, $R^3$, $R^4$, $R^5$, $R^6$, $R^7$, $R^8$, m and n are as previously defined except that neither $R^5$ and $R^6$ and $R^7$ and $R^8$ represent an oxygen atom, and $R^{32}$ represents a leaving group such as halo, for example chloro, bromo or iodo, or a sulphonate, for example methylsulphonate or p-toluenesulphonate, in the presence of a base.

Suitable bases of use in the reaction include inorganic bases such as alkali metal carbonates, for example, potassium carbonate.

Conveniently the reaction is effected in a suitable organic solvent, for example, dimethylformamide.

Compounds of formula (I) may also be prepared from different compounds of formula (I) by interconversion processes. In particular, interconversion processes may be used to vary the groups $R^3$ and $R^4$. For example, compounds of formula (I) wherein $R^3$ is other than H may be prepared from the corresponding compounds of formula (I) wherein $R^3$ is H by conventional methods, such as reaction with a compound $R^3$-Hal, where Hal represents halo, in the presence of a base. Suitable reagents and conditions will be readily apparent to those skilled in the art and are illustrated by the accompanying Examples. Suitable bases include organic bases, such as tertiary amines, e.g. triethylamine, and inorganic bases, such as alkali metal carbonates, e.g. sodium carbonate. Similarly, compounds of formula (I) wherein $R^4$ is $C_{1-6}alkyl$ or $COR^9$ may be prepared from compounds of formula (I) wherein $R^4$ is H by conventional alkylation or acylation procedures. Compounds of formula (I) wherein $R^3$ is $COR^9$ may also be prepared from compounds of formula (I) wherein $R^3$ is H by, for example, reaction with an appropriate acid anhydride. Compounds of formula (I) wherein $R^3$ is $C_{1-6}alkyl$ may be prepared from corresponding compounds of formula (I) wherein $R^3$ is $COR^9$ by reduction using, for example, borane or a borohydride such as sodium cyanoborohydride. Suitable procedures will be readily apparent to those skilled in the art. Compounds of formula (I) wherein $R^3$ is $C_{1-6}alkyl$ substituted by $CONR^{10}R^{11}$ may be prepared from corresponding compounds of formula (I) wherein $R^3$ is $C_{1-6}alkyl$ substituted by $CO_2R^{10}$ by treatment with ammonia or an amine of formula $NR^{10}R^{11}$.

Intermediates of formula (II) wherein $R^{30}$ is CHO (IIA) above may be prepared from corresponding compounds of formula (VI):

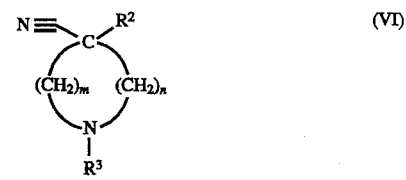

wherein $R^2$, $R^3$, m and n are as defined for formula (II) above by reduction. Suitable reducing agents will be readily apparent to one skilled in the art and include, for example, metallic hydrides, such as diisobutyl aluminium hydride.

The reaction is suitably carried out in an aqueous organic solvent, such as an ether, for example aqueous tetrahydrofuran.

Compounds of formula (II) wherein $R^{30}$ is $CR^5R^6NHR^4$ (IIB) may be prepared from intermediates of formula (IIA) or (IV) by reductive amination using conventional procedures.

Where they are not commercially available, the intermediates of formula (III) above may be prepared by the procedures described in the accompanying Examples or by alternative procedures which will be readily apparent to one skilled in the art.

Compounds of formula (IV) may be prepared from intermediates of formula (VI) by reaction with Grignard reagents of formula R⁷MgHal and/or R⁸MgHal, wherein Hal represents halo such as chloro, bromo or iodo, and, for compounds of formula (IV) where R⁴ is other than H, subsequent introduction of the group R⁴ onto the nitrogen atom by conventional methods.

Compounds of formula (V) are commercially available or may be prepared from commercially available compounds using conventional procedures.

Compounds of formula (VI) are commercially available, or may be prepared by known procedures.

Suitable methods for the preparation of compounds of formula (VI) are described in European Patent Application no. 0 337 167, *J. Am. Chem. Soc.*, 81, 1201 (1959), J. Med. Chem., 17, 453 (1974) and *J. Med. Chem.*, 24, 218 (1981).

For example, compounds of formula (VI) may be prepared from the corresponding carboxylic acids of formula (VII)

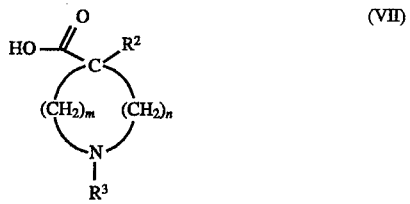

wherein $R^2$, $R^3$, m and n are as defined for formula (I) above by reaction with hydroxylamine and treatment with formic acid.

The reaction is preferably effected at elevated temperature.

In general, compounds of formula (VI) wherein $R^3$ is H and n is 0 may be prepared by cyclisation of an intermediate of formula (VIII)

wherein $R^2$, Hal and m are as previously defined, in the presence of a base.

Suitable bases of use in the reaction include tertiary amines, such as, for example, triethylamine. The reaction is conveniently effected in a suitable organic solvent, such as an ether, for example, tetrahydrofuran, suitably at elevated temperature, such as the reflux temperature of the chosen solvent.

Intermediates of formula (VIII) may be prepared by reaction of compounds of formula (IX) with compounds of formula (X)

wherein $R^2$, m and Hal are as previously defined, in the presence of a base, followed by convertion of the isonitrile function to an amine function under standard conditions.

Suitable bases of use in the reaction include alkali metal hydrides, such as, for example, sodium hydride. The reaction is conveniently effected in a suitable organic solvent, such as an ether, for example, tetrahydrofuran, suitably at elevated temperature, such as the reflux temperature of the chosen solvent.

Compounds of formulae (IX) and (X) are commercially available, or may be prepared from commercially available starting materials using conventional procedures well known to those skilled in the art.

Compounds of formula (VI) wherein n is other than 0 may in general be prepared from the corresponding compounds of formula (XI)

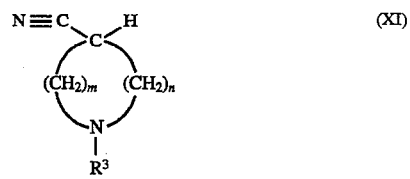

wherein $R^3$ and m are as previously defined and n is 1 or 2 by treatment with a base and reaction of the resulting nucleophile with a reagent suitable to introduce the group $R^2$, such as an activated aryl moiety, for example

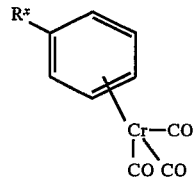

wherein $R^x$ is H or halo, such as chloro; an aryliodide in the presence of nickel bromide (*J. Am. Chem. Soc.*, 99, 4833 (1977)); or a hypervalent aryliodide (*Synthesis*, 709 (1984)).

Compounds of formula (XI) may be prepared from the corresponding intermediates of formula (XII)

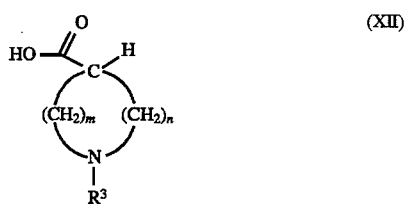

wherein $R^3$, m and n are as defined for formula (XI) above, as described for the preparation of compounds of formula (VI) from compounds of formula (VII).

Intermediates of formula (XII) may be prepared from compounds of formula (XIII)

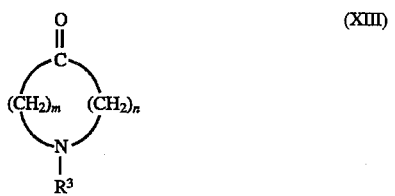

wherein $R^3$, m and n are as defined for formula (IX) by conventional methods, for example, by reaction with 1,3-dithiane and hydrolysis.

Still further procedures suitable for the preparation of compounds of formula (VI) will be readily apparent to those skilled in the art.

Compounds of the formula (I) wherein X is $NR^4$ and either $R^5$ and $R^6$ represent an oxygen atom or $R^7$ and $R^8$ represent an oxygen atom may be prepared by a process which comprises reacting a compound of formula (IIa) with a compound of formula (IIIa):

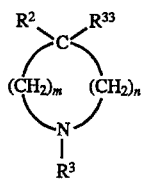

(IIa)

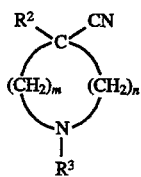

R³⁴—R¹ (IIIb)

wherein R¹, R², m and n are as defined for formula (I), R³ is as defined for formula (I) except that, when R³ is H it is replaced by a suitable protecting group, such as CO₂(C₁₋₆alkyl), and R³³ and R³⁴ are chosen as follows:

R³³ represents (C=O)OH and R³⁴ represents HNR⁴CR⁶R⁷; or

R³³ represents CR⁶R⁷NR⁴H and R³⁴ represents C(=O)Hal; or

R³³ represents NR⁴H and R³⁴ represents —N=C=O; or

R³³ represents —N=C=O and R³⁴ represents NR⁴H; or

R³³ represents O(C=O)Hal and R³⁴ represents NH₂; or

R³³ represents NH₂ and R³⁴ represents O(C=O)Hal;

wherein R⁴, R⁶ and R⁷ are as defined for formula (I) and Hal represents halo such as iodo, bromo or, preferably, chloro; followed by deprotection if, if required. In each case the reaction is effected under conventional conditions. For example, for the formation of an amide linkage the reaction is effected in the presence of a base. Favoured bases of use in the reaction include tertiary amines such as triethylamine and alkali metal carbonates such as potassium carbonate.

Intermediates of formula (IIa) above wherein R³³ is CR⁶R⁷NR⁴H and R⁴, R⁶ and R⁷ all represent H may be prepared from corresponding compounds of formula (IVa):

<image src="formula IV" />

(IV)

wherein R², R³, m and n are as defined for formula (II) above by reduction. Suitably reduction will be effected by catalytic hydrogenation, for example, using a nobel metal catalyst such as platinum, palladium or rhodium, or oxides thereof. A preferred catalyst is platinum dioxide which is preferably used under acidic conditions, for example, using acetic acid as solvent.

Compounds of formula (IIa) wherein R³³ is CR⁶R⁷NR⁴H and R⁶, R¹ and R⁴ are not all H may be prepared from intermediates of formula (IIa) by reductive amination using conventional procedures.

Compounds of formula (IIa) wherein R³³ is COOH or COHal are commercially available, or may be prepared by known procedures. For example, suitable methods are described in European Patent Application no. 0 337 167, *J. Am. Chem. Soc.*, 81, 1201 (1959), *J. Med. Chem.*, 17, 453 (1974) and *J. Med. Chem.*, 24, 218 (1981).

Compounds of formula (IIa) wherein R³³ is —N=C=O may be prepared from corresponding compounds of formula (IIa) wherein R³³ is NH₂ by reaction with triphosgene in the presence of a base, such as a tertiary amine, for example triethylamine.

Compounds of the formula (I) wherein X is SO or SO₂ may be prepared by oxidation of a compound of the formula (IIb):

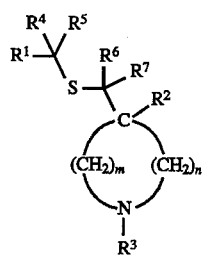

(IIb)

wherein R¹, R², R³, R⁴, R⁵, R⁶, R⁷, m and n are as defined for formula (I).

Suitable oxidising agents will be readily apparent to those skilled in the art and include peroxides, such as hydrogen peroxide and potassium permanganate, and peracids, such as m-chloroperbenzoic acid. For the preparation of a compound of formula (I) wherein X is SO, the appropriate intermediate of formula (II) is treated with one mole of oxidising agent. For the preparation of a compound of formula (I) wherein X is SO₂, the appropriate intermediate of formula (IIb) is treated with two moles of oxidising agent.

Alternatively, compounds of formula (I) wherein X is SO₂ may be prepared by oxidation of compounds of formula (I) wherein X is SO as above described. Intermediates of formula (IIb) may be prepared by a process which comprises reacting a compound of formula (IIIb) with a compound of formula (IVb):

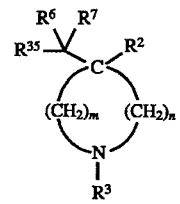

(IIIb)

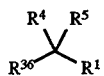

(IVb)

wherein R¹, R², R⁴, R⁵, R⁶, R⁷, m and n are as defined for formula (I), R³ is as defined for formula (I) except that, when R³ is H it is replaced by a suitable protecting group, such as CO₂(C₁₋₆alkyl); and one of R³⁵ and R³⁶ represents a leaving group and the other of R³⁵ and R³⁶ represents SH, in the presence of a base, followed by deprotection, if required.

Suitably R³⁵ represents a leaving group and R³⁵ represents SH.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide, sodium hydride or potassium hydride.

The intermediates of formula (IIIb) above wherein R³⁵ is SH may be prepared from the corresponding intermediates of formula (IIIb) wherein R³⁵ represents OH (hereinafter intermediates (IIIA)) by treating the latter compound with Lawesson's reagent or phosphorus pentasulphide in a suitable solvent, e.g. pyridine, at ambient or elevated temperatures, suitably at reflux temperature.

Intermediates of formula (IIIb) wherein R³⁵ is a leaving group may be prepared from intermediates of formula (IIIA) by conventional methods, such as treatment with an appropriate sulphonyl halide such as, for example, methanesulphonyl chloride or toluenesulphonyl chloride, or a thionyl halide.

Similarly, intermediates of formula (IVb) wherein $R^{36}$ is a leaving group may be prepared from the corresponding compounds of formula (IVb) wherein $R^{35}$ is OH by conventional methods.

Intermediates of formula (IVb) wherein $R^{36}$ is SH may be prepared from compounds of formula (Vb)

wherein $R^1$, $R^4$ and $R^5$ are as previously defined and $R^{37}$ represents an alkyl, alkoxy, aryl or aryloxy group, by hydrolysis.

Suitably the reaction is effected under base catalysis using, for example, an alkali metal alkoxide, such as sodium methoxide, in a suitable organic solvent such as an alcohol, for example, methanol.

Compounds of formula (Vb) may be prepared by reaction of compounds of formula $R^1CR^4R^5$-Hal, wherein $R^1$, $R^4$ and $R^5$ are as previously defined and Hal represents halo such as chloro, bromo or iodo, with compounds of formula $R^{37}COSH$, wherein $R^{37}$ is as previously defined, in the presence of a base.

Suitable bases of use in the reaction include alkali metal carbonates such as, for example, caesium carbonate.

Where the above-described process for the preparation of the compounds according to the invention gives rise to mixtures of stereoisomers these isomers may, if desired, be separated, suitably by conventional techniques such as preparative chromatography.

The novel compounds which contain one or more chiral centres may be prepared in racemic form, or individual enantiomers may be prepared either by enantiospecific synthesis or by resolution. For example, intermediate alcohols of formula (IIIA), wherein $R^{35}$ is OH, may be resolved into their component enantiomers by standard techniques, such as the formation of diastereomeric esters or amides, followed by chromatographic separation or separation by fractional crystallization and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of international application number PCT/GB92/01241. The compounds were found to be active with $IC_{50}$ at NKIR of less than 150 nM.

The compounds of this invention may be formulated as specifically illustrated at pages 35 to 36 of international application number PCT/GB92/01241.

The following examples illustrate this invention:

EXAMPLE 1

4-Phenyl-4-(2-Methoxybenzylaminomethyl)Piperidine Dihydrochloride a) N-$^t$Butoxycarbonyl-4-phenyl-4-cyanopiperdine Di-$^t$butyldicarbonate (20 g) was added to a stirred solution of 4-phenyl-4-cyano piperidine hydrochloride (20 g) and $Et_3N$ (9.5 g) in dry dichloromethane (100 ml). The resulting solution was stirred for 18 hours at room temperature. The reaction mixture was washed with water (100 ml) and the organic layer separated and dried over $MgSO_4$. Filtration and removal of solvent under reduced pressure afforded a white solid. Recrystallisation from hexane gave the title compound as white needles, mp=64° C. $^1H$ NMR (360 MHz, $CDCl_3$) δ 1.46 (9H, s, C($\underline{CH}_3$)$_3$), 1.90 (2H, m, C—C$\underline{H}$H and C$\underline{H}$H—C), 2.04 (2H, m, C—C$\underline{H}$H and CH$\underline{H}$—C), 3.20 (2H, m, N—C$\underline{H}$H and C$\underline{H}$H—N), 4.26 (2H, m, N—CH$\underline{H}$ and CH$\underline{H}$—N), 7.26–7.49 (5$\underline{H}$, m, Ar $\underline{H}$); MS (CI$^+$) 287 (M+H$^+$).

b) N-$^t$Butoxycarbonyl-4-phenyl piperidine-4-carboxaldehyde

A solution of N-$^t$Butoxycarbonyl-4-phenyl-4-cyano piperidine (5.0 g) in dry toluene (100 ml) at −78° C. was treated with a solution of DIBALH (27.7 ml×1.0 mol) in toluene. The reaction was maintained at −78° C. for two hours, at which time it was quenched by slow addition of a saturated solution of $NH_4Cl$ (20 ml), and allowed to warm to room temperature. The reaction mixture was poured into water (100 ml) and extracted into ethyl acetate. The organic layers were separated, dried over $MgSO_4$, filtered and solvent removed to give a yellow oil. Flash chromatography in silica gel (20% EtOAc in hexane) afforded the product as a clear oil (2.1 g). $^1H$ NMR (360 MHz, $CDCl_3$) δ 1.45 (9H, s, C($\underline{CH}_3$)$_3$), 1.95 (2H, m, C—C$\underline{H}$H and C$\underline{H}$H—C), 2.07 (2H, m, C—CH$\underline{H}$ and CH$\underline{H}$—C), 3.12 (2H, m, N—C$\underline{H}$H and C$\underline{H}$H—N), 3.85 (2H, m, N—CH$\underline{H}$ and CH$\underline{H}$—N), 7.26–7.40 (5H, m, Ar H), 9.40 (1H, s, C$\underline{H}$O); MS (CI$^+$) 290 (M+H$^+$).

c) N-$^t$Butoxycarbonyl-4-phenyl-4-(2-methoxybenzyl aminomethyl)piperidine

A solution of N-$^t$butoxycarbonyl-4-phenylpiperidine-carboxaldehyde (500 mg) and 2-methoxybenzylamine (246 mg) in toluene (50 ml) was warmed to reflux under Dean and Stark conditions for 24 hours. After cooling to room temperature the solvent was removed under reduced pressure, and the residue re-dissolved in dry MeOH (20 ml). The pH was adjusted to 4 by the addition of solid citric acid, and $NaCNBH_3$ (258 mg) added. The reaction was allowed to stir at room temperature for four hours, at which time the solvent was removed under reduced pressure. The solid residue was dissolved in water, basified to pH 10 and extracted into ethyl acetate. The organic layers were separated, dried over $MgSO_4$, filtered and solvent removed to afford a clear oil. Flash chromatography on silica gel (5% MeOH/$CH_2Cl_2$) afforded the title compound as a clear oil (400 mg). $^1H$ NMR (360 MHz, $CDCl_3$) δ 1.42 (9H, C($\underline{CH}_3$)$_3$), 1.79 (2H, m, C—C$\underline{H}$H and C$\underline{H}$H—C), 2.04 (2H, m, C—CH$\underline{H}$ and CH$\underline{H}$—C), 2.65 (2H, s, $CH_2$NH—$\underline{CH}_2$Ar), 3.14 (2H, m, N—C$\underline{H}$H and C$\underline{H}$H—N), 3.60 (2H, s, $\underline{CH}_2$—NH—$CH_2$Ar), 3.76 (2H, m, N—CH$\underline{H}$ and CH$\underline{H}$—N), 3.77 (3H, s, OCH$_3$), 6.71 (1H, d, J=6.0 Hz, H-6'), 6.85 (1H, t, J=6.0 and 1.0 Hz, H-5'), 7.06 (1H, d, J=6.0Hz, H-3'), 7.17 (1H, t, J=6.0 and 1.0 Hz, H-4'), 7.20–7.46 (5H, m, Ar $\underline{H}$); MS (CI$^{30}$) 411 (M+H$^+$).

d) 4-Phenyl-4-(2-methoxybenzylaminomethyl)piperidine dihydrochloride

Dry HCl gas was passed through a solution of N-$^t$butoxycarbonyl-4-phenyl-4-(2-methoxybenzylaminomethyl)piperidine (400 mg) in dry ether (50 ml) at 0° C. for 30 minutes. The passage of gas was stopped and the solution allowed to warm to room temperature and stirred for 2 hours. The white precipitate was filtered off and re-crystallised from ethyl acetate to afford the title compound as white needles. Mp=78°–80° C. $^1H$ NMR (360 MHz, DMSO) δ 2.14 (2H, m, C—CH and CHH—C), 2.37 (2H, m, C—CHH and CHH—C), 2.69 (2H, s, N—CHH and CHH—N), 2.78 (2H, m, N—CHH and CHH—N), 3.19 (2H, s, CH$_2$—NH—CH$_2$), 3.33 (2H, s, CH$_2$—NH—CH$_2$Ar), 3.57 (3H, s, OCH$_3$), 6.91 (1H, d, J=6.0 Hz, H-6'), 6.96 (1H, t, J=6.0 and 1.0 Hz, H-5'), 7.25 (1H, d, J=6.0 Hz, H-3'), 7.37 (1H, t, J=6.0 and 1.0 Hz, H-4'), 7.41–7.73 (5H, m, Ar H); MS (CI$^+$) 311 (M+H$^+$); C$_{20}$H$_{27}$N$_2$O.2HCl.H$_2$O requires C, 59.70; H, 7.77; N, 6.96. Found: C, 59.36; H, 7.95; N, 6.80%.

EXAMPLE 2

4-Phenyl-4-[(3,5-Bistrifluoromethylbenzyl)amido]methyl] piperidine Hydrochloride a) 4-Phenyl-4-Aminomethyl-1-t-Butoxycarbonyl Piperidine A solution of the compound of Example 1, part A in 15% acetic acid ethanol was hydrogenated at 50 psi over platinum dioxide (0.5 g) for 18 hours. The catalyst was filtered off and the solvent removed under reduced pressure. The residue was partitioned between ethyl acetate and 2N sodium hydroxide solution. The organic extract was separated, dried (MgSO$_4$), filtered and the solvent removed under reduced pressure to afford the pure product as a clear off. $^1$HNMR (360 MHz, CDCl$_3$) δ 1.45 (9H, s, (CH$_3$)$_3$C), 1.67 (2H, m, CHH—CH$_2$N×2), 2.20 (2H, m, CHH—CH$_2$N×2), 2.75 (2H, brs, CH$_2$NH$_2$), 3.05 (2H, m, CH$_2$CHHN×2), 3.71 (2H, m, CH$_2$CHHN×2), 7.21–7.39 (5H, m, ArH); MS CI$^+$ 291 (M+1)$^+$.

b) 4-Phenyl-4-[(3,5-Bistrifluoromethylbenzyl)amido]methylpiperidine Hydrochloride 3,5-Bistrifluoromethylbenzoylchloride (110 mg) was added to a stirred solution of 4-phenyl-4-aminomethyl-1-t-butoxycarbonyl piperidine (118 mg) and triethylamine (55 μl) in dry dichloromethane at room temperature. After two hours the reaction mixture was washed with water, the organic layer separated and dried (MgSO$_4$). Filtration and removal of solvent afforded yellow crystals. Recrystallisation from hexane, followed by deprotection using ethereal hydrogen chloride afforded the product as a white solid (172 mg), mp 215°–216° C. $^1$H NMR (360 MHz, DMSO-d$_6$) δ 2.07 (2H, m, CHH—CH$_2$N×2), 2.31 (2H, m, CHH—CH$_2$N×2), 2.68 (2H, m, CH$_2$—CHHN×2), 3.22 (2H, m, CH$_2$—CHHN×2), 3.42 (2H, s, CH$_2$N—CO), 7.27–7.46 (5H, ArH), 8.31 (1H, s, CF$_3$C—CH—CCF$_3$), 8.38 (2H, s, C—CH—CCF$_3$×2); MS CI$^+$ 431 (M+1)$^+$; C$_{21}$H$_{20}$N$_2$O. HCl. ½H$_2$O requires C, 53.00; H, 4.62; N, 5.89; Found C, 53.09; H, 4.24; N, 5.81%.

EXAMPLE 3

1-t-Butoxycarbonyl-4-phenyl-4-[3,5-bis(trifluoromethyl)benzylthiomethyl]piperidine a) Thioacetic acid (5.13 ml) was added to a suspension of caesium carbonate (11.7 g) in dimethylformamide (120 ml) at room temperature. The solution was stirred for 10 min and a solution of 3,5-bis(trifluoromethyl)benzyl bromide (20 g) in dimethylformamide (10 ml) was added. The resulting solution was stirred for 16 h, in the dark. The solvent was removed in vacuo and the residue was partitioned between ethyl acetate and water. The organic layer was washed with water, dried (Na$_2$SO$_4$) and the solvent was removed leaving an orange oil. The off was chromatographed on silica gel in 5% ethyl acetate/petrol giving 3,5-bis(trifluoromethyl)benzyl thioacetate (14.8 g) as a yellow oil. $^1$H NMR (360 MHz, CDCl$_3$) δ 2.39 (3H, s), 4.17 (2H, s), 7.75 (3H, s); m/z (CI$^+$) 303 (M$^+$+1).

b) Sodium methoxide (3 g) was added in small portions to a solution of 3,5-bis(trifluoromethyl)benzyl thioacetate (10 g) in methanol (50 ml), under an inert atmosphere. The resulting solution was stirred at room temperature for 16 h. The solvent was removed and the residue was partitioned between ethyl acetate and 0.1N HCl solution. The organic layer was dried (Na$_2$SO$_4$) and the solvent was removed leaving a clear oil which was chromatographed on silica in 2% ethyl acetate/petrol. 3,5-Bis(trifluoromethyl)benzyl mercaptan (5.02 g) was obtained as an off white solid (STENCH).

c) 4-Phenyl-4-carboxyl piperidine tosylate (20 g) was suspended in tetrahydrofuran (50 ml). Lithium aluminium hydride (1M solution in tetrahydrofuran, 106 ml) was added dropwise to the suspension at 0° C. When the addition was complete the solution was stirred at reflux temperature for 2 h. The temperature was lowered to room temperature and 2N sodium hydroxide solution (6.4 ml) was added with extreme care, followed by water (8 ml) and a further 9.5 ml of 2N sodium hydroxide solution. Di-t-butyl-dicarbonate (11.56 g) in dichloromethane (65 ml) was added and the resulting slurry was stirred for 16 h at room temperature. The slurry was filtered through Na$_2$SO$_4$ and washed with dichloromethane (2.5 L). The solvent was removed giving a clear viscous oil which was recrystallized from ether-petrol giving 1-t-butoxycarbonyl-4-phenyl-4-hydroxymethyl piperidine (12.4 g) as a white solid. mp 64° C. MS CI$^+$ 287 (M+1)$^+$.

d) Triethylamine (5.25 ml) was added to a solution of 1-t-butoxycarbonyl-4-phenyl-4-hydroxymethyl piperidine (10 g) in dichloromethane (200ml). The temperature was lowered to 0° C. and methane sulphonyl chloride (2.92 ml) was added. The solution was stirred for 30 min, washed with water, dried (Na$_2$SO$_4$), and the solvent was removed giving a clear oil. The oil was recrystallised from ethyl acetate/petrol giving N-t-butoxycarbonyl-4-phenylpiperidin-4-yl)methyl methanesulphonate (11.65 g) as a white solid. m/z (CI$^+$) 387 (M$^+$+NH$_4^+$).

e) A solution of 3,5-bis(trifluoromethyl)benzyl mercaptan, (2 g) in N-methyl pyrollidinone (10 ml) was added dropwise to a stirred suspension of sodium hydride (80% dispersion, 325 mg) in N-methyl pyrollidinone (30 ml) at room temperature. The solution was stirred for 1 h. N-t-butoxycarbonyl-4-phenylpiperidin-4-yl)methyl methanesulphonate (2.5 g) was added and the solution was stirred for 16 h at 60° C. The solution was allowed to cool to room temperature, poured into water, extracted twice with ethyl acetate. The organic layer was washed with water, dried (Na$_2$SO$_4$), and the solvent was removed in vacuo giving a brown oil which was chromatographed on silica gel in 15% ethyl acetate/petrol. 1-t-Butoxycarbonyl-4-phenyl-4-[3,5-bis(trifluoromethyl)benzylthiomethyl]piperidine (2.84 g) was obtained as a clear oil. m/z (CI$^+$) 534 (M$^+$+1).

EXAMPLE 4

1-t-Butoxycarbonyl-4-phenyl-4-[3,5-bis(trifluoromethyl)benzylsulphinylmethyl]piperidine m-Chloroperoxybenzoic acid (80–90%, 0.4 g) was added to a solution of Example 3 (1 g) in dichloromethane (20 ml) containing potassium carbonate (0.5 g), at 0° C. The solution was stirred for 30 min, diluted with dichloromethane (20 ml), washed with water, dried (Na$_2$SO$_4$) and removal of the solvent in vacuo gave an off white solid. The solid was recrystallised from diethyl ether/petrol giving 1-t-butoxycarbonyl-4-phenyl-4-[3,5-bis(trifluoromethyl)benzylsulphinylmethyl]piperidine as a white solid, m.p. 123°–134° C., m/z (CI$^+$) 567 (M$^+$+NH$_4^+$). Found: C, 57.00; H, 5.18; N, 2.36. C$_{26}$H$_{29}$NO$_3$SF$_6$ requires C, 56.82; H, 5.32; N, 2.55.

EXAMPLE 5

1-t-Butoxycarbonyl-4-phenyl-4-[3,5-bis(trifluoromethyl) benzylsulphonylmethyl]piperidine m-Chloroperoxybenzoic acid (80–90%, 0.4 g) was added to a solution of Example 3 (0.45 g) in dichloromethane (15 ml) containing sodium bicarbonate (0.5 g), at 0° C. The solution was stirred for 5 h at room temperature, diluted with dichloromethane (15 ml), washed with water, dried ($Na_2SO_4$) and the solvent was removed. Butoxycarbonyl-4-phenyl-4-[3,5-bis(trifluoromethyl) benzylsulphonylmethyl] piperidine was obtained as a yellow foam. m/z ($CI^+$) 534 $(M+1)^+$.

EXAMPLE 6

4-Phenyl-4-[3,5-bis(trifluoromethyl)benzylsulphonyl methyl]piperidine hydrochloride 1t-Butoxycarbonyl-4-phenyl-4-[3,5-bis(trifluoromethyl) benzylsulphonyl methyl]piperidine was dissolved in diethyl ether (5 ml) and ethereal HCl (5 ml) was added. The solution was left standing for 16 h, solvent was removed and residue was recrystallised from isopropyl alcohol/isopropyl ether giving 4-phenyl-4-[3,5-bis(trifluoromethyl) benzylsulphonylmethyl]piperidine hydrochloride (196 mg) as a white solid, m.p. 249° C. (dec), m/z ($CI^+$) 466 ($M^+$+1). Found: C, 49.90; H, 4.36; N, 2.89. $C_{21}H_{21}NO_2SF_6$. HCl requires C, 50.25; H, 4.42; N, 2.79.

EXAMPLE 7

4-Phenyl-4-[(3,5-bistrifluoromethyl)benzylaminomethyl] piperidine dihydrochloride A solution of 3,5-bistrifluoromethylbenzyl bromide (1.86 ml) in dry $CH_2Cl_2$ was added dropwise to a chilled solution of 4-phenyl-4-aminomethyl-1-t-butoxycarbonyl piperidine (2.46 g). in dry $CH_2Cl_2$. The reaction was allowed to warm to room temperature and stirred for two hours, diluted with water (50 ml), the organic layer separated and dried over ($MgSO_4$). Filtration and removal of solvent afforded a yellow oil, which was further purified by MPLC ($SiO_2$/EtOAc/nHex). The recovered product was treated with HCl/$Et_2O$ for 18 hrs. The solvent was removed under reduced pressure and the product recrystallised from EtOAc. mp 210°–215° C.; $C_{21}H_{22}N_2F_6$.2HCl.½$H_2O$ requires C, 50.61; H, 5.06; N, 5.62; Found C, 50.24; H, 5.14; N, 5.70%.

EXAMPLE 8

4-Phenyl-4-[(3.5-dichloro)benzylaminomethyl]piperidine hydrochloride

The title compound was prepared by the method of Example 4. mp 220°–223° C.; $C_{19}H_{22}N_2Cl_2$.1.5HCl requires C, 56.48; H, 5.86; N, 6.93; Found C, 56.28; H, 5.50; N, 6.60%.

EXAMPLE 9

4-Phenyl-4-[(3,5-dichloro)benzylamino-1-ethyl]piperidine dihydrochloride

The title compound was prepared by the method of Example 4. mp 200°–208° C.; $C_{20}H_{24}N_2Cl_2$.2HCl requires C, 55.60; H, 6.01; N, 6.42; Found C, 54.91; H, 6.10; N, 6.30%.

EXAMPLE 10

4-Phenyl-4-[(3-isopropoxy)benzamidomethyl) piperidine hydrochloride

The title compound was prepared by the method of Example 2. mp 124°–125° C. m/z ($CI^+$) 353 $(M+H)^+$.

EXAMPLE 11

4-Phenyl-4-[(3-isopropoxy) N-methyl-benzamidomethyl) piperidine hydrochloride

Methyl iodide (1.0 g) was added to a stirred solution of NaH (44 mg×60%) and the compound of Example 7 (240 mg) in dry DMF. The resulting solution was stirred for 18 hrs at room temperature. The reaction was then diluted with water and extracted into EtOAc. The organic layers were separated and dried over ($MgSO_4$). Filtration and removal of solvent afforded a clear oil. Purification by MPLC ($SiO_2$/EtOAc/nHex) followed by treatment with $Et_2O$/HCl and recrystallisation from EtOAc afforded the title compound. mp 210°–211° C.; $C_{23}H_{30}N_2O_2$.HCl·2$H_2O$ requires C, 62.93; H, 8.03; N, 6.38; Found C, 63.37; H, 8.09; N, 6.63%.

We claim:

1. A compound of the formula (I), or a pharmaceutically acceptable salt thereof:

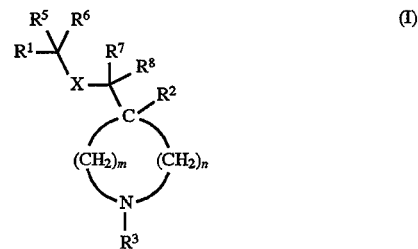

wherein:

X is $NR^4$ or SO or $SO_2$ m is 2, 3 or 4;

n is 0, 1 or 2, with the proviso that the sum of m+n is 4;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, SO $R^a$, —$NR^aR^b$, —$NR^aCOR^b$, —$NR^aCO$ $R^b$, —CO $R^a$, —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, SO $R^a$, —$NR^aR^b$, —$NR^aCOR^b$, —$NR^aCO$ $R^b$, —$CO_2$ $R^a$ or —$CONR^aR^b$, where $R^a$ and $R^b$ each independently represent H, $C_{1-6}$alkyl, phenyl or trifluoromethyl; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or difluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONHphenyl(C_{1-4}alkyl)$, $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), Y—$R^{16}$ or CO—Z—$(CH_2)_q$—$R^{12}$;

$R^4$ represents H, $C_{1-6}$alkyl or $COR^9$;

$R^5$, $R^6$, $R^7$ and $R^8$ each independently represent H or $C_{1-6}$alkyl;

$R^9$ represents H, $C_{1-6}$alkyl or phenyl;

$R^{10}$ and $R^{11}$ each independently represent H or $C_{1-6}$alkyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, trifluoromethyl or phenyl optionally substituted by one or more substituents selected from $C_{1-6}$alkyl, $C_{1-6}$alkoxy, halo and trifluoromethyl;

$R^{16}$ represents an optionally substituted aromatic heterocycle;

Y represents a hydrocarbon chain of 1,2,3 or 4 carbon atoms which may optionally be substituted by oxo; with the exception of:

1-(2-(4-chlorophenyl)ethyl)-4-phenyl-4-[(4-chlorobenzyl)aminomethyl]piperidine;
1-butyl-4-phenyl-4-[(2-hydroxybenzyl)aminomethyl]piperidine;
1-butyl-4-phenyl-4-[(4-hydroxybenzyl)aminomethyl]piperidine;
1-butyl-4-phenyl-4-[(4-chlorobenzyl)aminomethyl]piperidine;
1-butyl-4-phenyl-4-[(4-aminobenzyl)aminomethyl]piperidine;
1-butyl-4-phenyl-4-[(3,4,5-trimethoxybenzyl)aminomethyl]piperidine;
4-[(benzylamino)methyl]-1-methyl-4-phenyl-piperidine.

2. The compound of claim 1 wherein:
X is SO or $SO_2$.

3. The compound of claim 1 wherein:
$R^5$, $R^6$, $R^7$ and $R^8$ are each H, or $R^5$ is methyl and $R^6$, $R^7$ and $R^8$ are each H.

4. The compound of claim 1 wherein m is 2 and n is 2.

5. The compound of claim 1 wherein $R^3$ is H or Y—$R^{16}$.

6. The compound of claim 5 wherein $R^3$ is Y—$R^{16}$ wherein Y is an alkyl group of 1 to 4 carbon atoms and $R^{16}$ is an unsubstituted 5-membered nitrogen containing heterocycle or a 5-membered nitrogen containing heterocycle substituted by oxo.

7. The compound of claim 1 of the formula (Ia), or a pharmaceutically acceptable salt thereof:

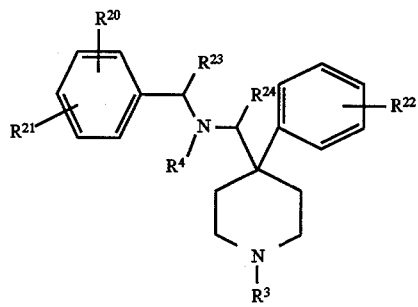

(Ia)

wherein:

$R^3$ and $R^4$ are as defined in claim 1;

$R^{20}$ and $R^{21}$ are independently selected from: H, $C_{1-6}$ alkyl, $C_{2-6}$ alkenyl, $C_{2-6}$ alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, $NR^aCO_2R^b$, $COR^a$, or —$CONR^aR^b$, wherein $R^a$ and $R^b$ are as defined in claim 1;

$R^{22}$ is H or halo;

$R^{23}$ and $R^{24}$ are independently selected from H and methyl.

8. The compound of claim 7 wherein $R^{22}$ is H or fluoro.

9. The compound of claim 7 wherein $R^3$ is H or Y—$R^{16}$.

10. The compound of claim 9 wherein $R^3$ is Y—$R^{16}$ wherein Y is an alkyl group of 1 to 4 carbon atoms and $R^{16}$ is an unsubstituted 5-membered nitrogen containing heterocycle or a 5-membered nitrogen containing heterocycle substituted by oxo.

11. A compound which is selected from the group consisting of:

4-Phenyl-4-(2-Methoxybenzylaminomethyl)piperidine;

1-t-Butoxycarbonyl-4-phenyl-4-[3,5-bis(trifluoromethyl)benzylsulphinylmethyl]piperidine;

1-t-Butoxycarbonyl-4-phenyl-4-[3,5-bis(trifluoromethyl)benzylsulphonylmethyl]piperidine;

4-Phenyl-4-[3,5-bis(trifluoromethyl)benzylsulphonylmethyl]piperidine;

4-Phenyl-4-[(3,5-bistrifluoromethyl)benzylaminomethyl]piperidine;

4-Phenyl-4-[(3,5-dichloro)benzylaminomethyl]piperidine;

4-Phenyl-4-[(3,5-dichloro)benzylamino-1-ethyl]piperidine;

and pharmaceutically acceptable salts thereof.

12. A pharmaceutical composition comprising a compound of claim 1 or a pharmaceutically acceptable salt thereof in association with a pharmaceutical carrier therefor.

13. A method for the treatment or prevention of physiological disorders associated with an excess of tachykinins which comprises administering to a patient in need thereof a tachykinin reducing amount of the compound of claim 1 or a pharmaceutically acceptable salt thereof.

* * * * *